US009839657B2

(12) United States Patent
Deaton et al.

(10) Patent No.: US 9,839,657 B2
(45) Date of Patent: Dec. 12, 2017

(54) PREBIOTIC COMPOSITIONS COMPRISING ONE OR MORE TYPES OF BACTERIOPHAGE

(71) Applicant: DEERLAND ENZYMES, INC., Kennesaw, GA (US)

(72) Inventors: John Deaton, Kennesaw, GA (US); Elizabeth Ertle, Kennesaw, GA (US); Hilton Grant Dawson, North Fort Meyers, FL (US)

(73) Assignee: DEERLAND ENZYMES, INC., Kennesaw, GA (US)

( * ) Notice: Subject to any disclaimer, the term of this patent is extended or adjusted under 35 U.S.C. 154(b) by 263 days.

(21) Appl. No.: 14/439,866

(22) PCT Filed: Mar. 8, 2013

(86) PCT No.: PCT/US2013/029796
§ 371 (c)(1),
(2) Date: Apr. 30, 2015

(87) PCT Pub. No.: WO2014/070225
PCT Pub. Date: May 8, 2014

(65) Prior Publication Data
US 2015/0297648 A1   Oct. 22, 2015

Related U.S. Application Data

(60) Provisional application No. 61/720,121, filed on Oct. 30, 2012.

(51) Int. Cl.
| | | |
|---|---|---|
| *A61K 35/745* | (2015.01) | |
| *A61K 35/76* | (2015.01) | |
| *C12N 1/20* | (2006.01) | |
| *C12N 7/00* | (2006.01) | |
| *A61K 35/742* | (2015.01) | |
| *A61K 35/744* | (2015.01) | |
| *A61K 35/747* | (2015.01) | |

(52) U.S. Cl.
CPC ............ *A61K 35/76* (2013.01); *A61K 35/742* (2013.01); *A61K 35/744* (2013.01); *A61K 35/745* (2013.01); *A61K 35/747* (2013.01); *C12N 1/20* (2013.01); *C12N 7/00* (2013.01); *C12N 2795/00032* (2013.01)

(58) Field of Classification Search
None
See application file for complete search history.

(56) References Cited

U.S. PATENT DOCUMENTS

| | | | |
|---|---|---|---|
| 5,968,569 A | 10/1999 | Cavadini et al. | |
| 6,461,608 B1 | 10/2002 | Averback et al. | |
| 7,951,575 B2 | 5/2011 | Bruessow et al. | |
| 8,021,657 B2 | 9/2011 | Bruessow et al. | |
| 2005/0106132 A1 | 5/2005 | Porubcan | |
| 2011/0189132 A1 | 8/2011 | Garner et al. | |
| 2012/0009154 A1 | 1/2012 | Porubcan et al. | |

OTHER PUBLICATIONS

Minot et al., The human gut virome: Inter-individual variation and dynamic response to diet, Genome Res. 2011 21: 1616-1625.*
Breitbart et al., Metagenomic Analyses of an Uncultured Viral Community from Human Feces, Journal of Bacteriology, Oct. 2003, p. 6220-6223.*
International Search Report and Written Opinion for PCT/US2013/029796 dated Jul. 26, 2013.
International Preliminary Report on Patentability for PCT/US2013/029796 dated May 14, 2015.
Bhowmik, et al., "Probiotic Efficiency of Spirulina Platensis-Stimulating Growth of Lactic Acid Bacteria," World Journal of Dairy & Food Sciences 4:160-163, 2009.
Chen, et al., "Optimization of the Growth Rate of Probiotics in Fermented Milk Using Genetic Alhorithms and Sequential Quadratic Programming Techniques", Asian-Autralasian Journal of Animal Sciences, vol. 16, No. 6, 2003.
Delbrück, et al., "Bacterial viruses or bacteriophages," Biol. Rev. 21:30-40, 1946.
Demerec, et al., "Bacteriophage-resistant mutants in *Escherichia coli*," Genetics 30:119-136, 1944.
Durmaz, et al., "Prevalence of Enterotoxigenic Bacteroides fragilis in Patients with Diarrhea: a Controlled Study," Anaerobe 11(6):318-321, 2005.
Eckburg, et al., "Diversity of the Human Intestinal Microbial Flora", Science. 14(308):1635-1638, 2005.
Gibson, et al., "Selective Stimulation of Bifidobacteria in the Human Colon by Oligofructose and Inulin," Gastroenter 108:975-982, 1995.
Guarner, et al., "Gut flora in health and disease," Lancet 361(9356):512-519, 2003.
Guttman, et al., "Basic phage biology. In: Bacteriophages: Biology and Applications", Kutter E andSulakvelidze A (eds). New York: CRC Press, pp. 29-66, 2005.
Klieve, et al., "Morphological diversity of ruminal bacteriophages from sheep and cattle," Appl Environ Microbiol 54(6):1637-1641, 1988.
Moore, et al., "Intestinal flora in health and disease," Gastroenterology 86:174-193, 1984.
Moore, et al., "Some current concepts in intestinal bacteriology", Am. J. Clin. Nutr. 31:33-42, 1978.
Ofek, et al., "Anti-adhesion Therapy of Bacterial Diseases", FEMS Immunol Med Microbiol 38:181-191, 2003.
Orpin, et al., "The occurrence of bacteriophages in the rumen and their influence on rumen bacterial population," Experientia 30:1018-1020, 1974.

(Continued)

*Primary Examiner* — Suzanne M Noakes
*Assistant Examiner* — Stephen Chong
(74) *Attorney, Agent, or Firm* — Meunier Carlin & Curfman LLC

(57) ABSTRACT

Disclosed herein are compositions that comprise one or more types of bacteriophage and methods of using such bacteriophages as a prebiotic to promote the growth of beneficial bacteria by decreasing harmful bacterial populations and releasing nutrients into the environment for good bacteria in the digestive system of an individual.

11 Claims, 1 Drawing Sheet

(56) References Cited

OTHER PUBLICATIONS

Quintero, et al., "Adherence Inhibition of Cronobacter Sakazakii and Other Pathogens by Prebiotic Oligosaccharides, Plant Extracts, and Other Naturally Derived Molecules," Dissertations & Theses in Food Science and Technology, University of Nebraska 62:1448-1454, 2011.
Rakieten, et al., "Studies with bacteriophages active against mucoid strains of bacteria," J. Bacteriol. 40:529-545, 1940.
Russo et al., "Beta-Glucan Improve Growth, Viability and Colonization of Probiotic Microorganisms," International Journal of Molecular Sciences 13:6026-6039, 2012.
Vasile et al., "Growth and Cell Viability Improve of the Probiotic Strain *Lactobacillus casei* SSP.Paracasei in the Presence of Oat Bran and Buckwheat Flour," Innovative Romanian Food Biotechnology 9:52-59, 2011.

\* cited by examiner

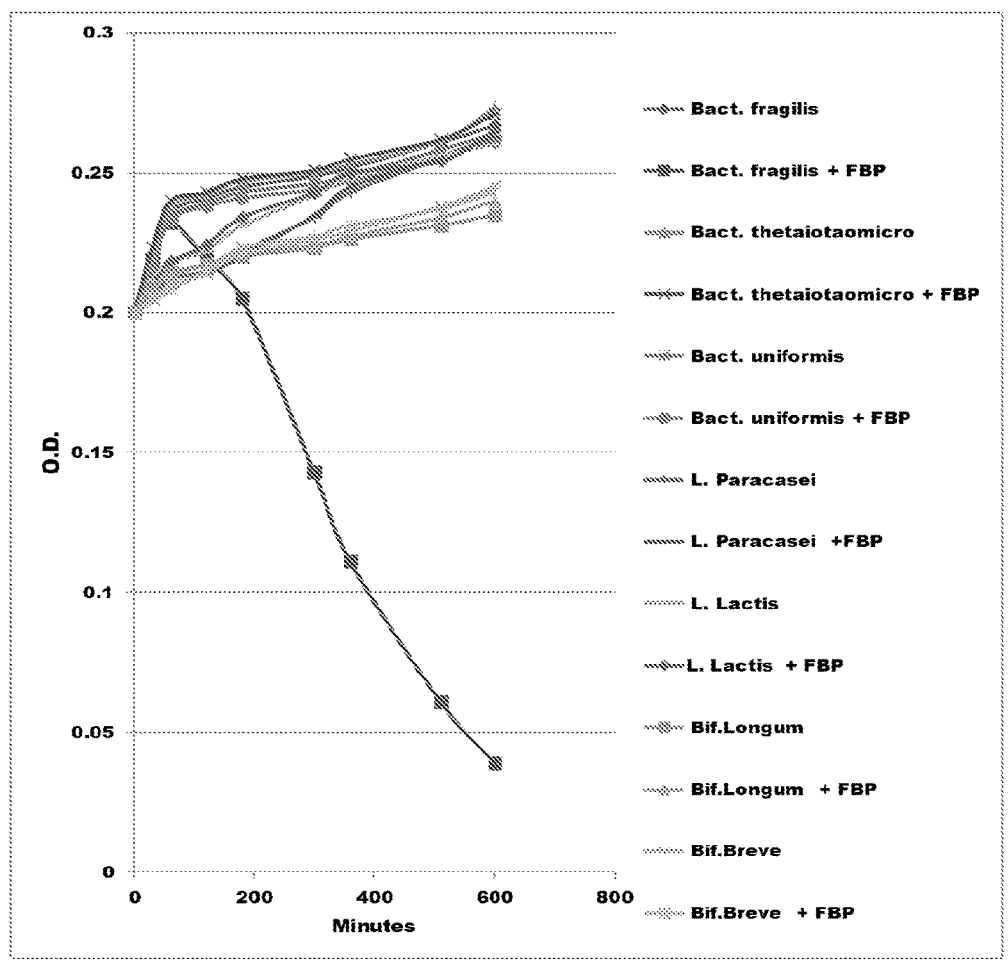

PREBIOTIC COMPOSITIONS COMPRISING ONE OR MORE TYPES OF BACTERIOPHAGE

FIELD

Disclosed herein are compositions that comprise one or more types of bacteriophage and methods of using such bacteriophages as a prebiotic to promote the growth of beneficial bacteria by decreasing harmful bacterial populations and releasing nutrients into the environment for good bacteria in the digestive system of an individual.

BACKGROUND

Microflora populations containing disproportionate concentrations of undesirable organisms can be treated with antibiotics or cleansing regimes to eliminate most of the organisms in the gut, both desirable and undesirable, followed by probiotic supplement to reestablish microflora balance. High doses of probiotics, consumed in the form of fermented foods containing the active probiotic organism or as nutritional supplements containing a specific minimum colony count of the probiotic are somewhat effective in controlling undesirable organisms. To be effective, large doses of the probiotic must be taken regularly to establish and to maintain colonization and to overcome the adverse environment created by undesirable organisms (Handbook of Prebiotics and Probiotics Ingredients, CRC Press, Boca Raton, Fla. 2009).

To assist in establishing probiotic colonization in the presence of large established populations of undesirable organisms, prebiotics, which are usually non-digestible carbohydrates can be used. These carbohydrate are selected for their ability to feed the probiotic organism preferentially and/or inhibit the growth or the undesirable organism. Id.

Another mechanism which has been described for prebiotic function is inhibition of adhesion by undesirable microorganism to the intestinal wall (Quintero, M. I., "Adherence Inhibition of *Cronobacter Sakazakii* and Other Pathogens By Prebiotic Oligosaccharides, Plant Extracts, and Other Naturally Derived Molecules," Dissertations & Theses in Food Science and Technology, University of Nebraska, Lincoln, Apr. 22, 2011). When adverse organisms are able to adhere and establish colonization, they modify the local environment to enhance its survival and to inhibit the colonization by competing with desirable organisms. Certain non-fermentable carbohydrates have structures resembling those found in the surface of epithelial cells. These prebiotics bind to the undesirable bacteria preventing it from adhering to the intestinal wall and allowing the organism to pass out of the digestive tract. Of course once the organism is attached to the intestinal wall, the prebiotic may be ineffective in dislodging it.

The major products of probiotic metabolism are short chain fatty acids (SCFAs), the gases hydrogen and carbon dioxide, and bacterial cell mass. Unwanted symptoms relating to gas production in the gut are widely reported in human prebiotic feeding studies including flatulence, bloating and diarrhea. Increased cell mass and unutilized prebiotic carbohydrate can produce an undesired laxative effect by stimulation of peristalsis due to the increased bowel content (Gibson, G. R., et al., "Selective Stimulation of Bifidobacteria in the Human Colon by Oligofructose and Inulin," *Gastroenter* 108:975-982, 1995).

In addition to polysaccharides, certain proteins and peptides and lipids also improve the growth of probiotics by inhibiting the undesirable organisms. Examples are lactoferrin, proanthocyanidins, and a high molecular weight component of cranberry juice. These materials may have several mechanisms which inhibit colonization by undesirable organisms including inhibition of adherence. (Ofek I., et al., "Anti-adhesion Therapy of Bacterial Diseases," *FEMS Immunol Med Microbiol* 38:181-191, 2003.) These materials are quite expensive and require high concentrations to be effective and their specificity may be more broad spectrum antibiotic than desired.

What are needed are new compositions for increasing the growth of desirable microflora. The methods and compositions disclosed herein accomplish this goal by administering one or more bacteriophage, which lyse specific harmful and undesirable bacteria thus decreasing specific bacterial populations and thereby adding nutrients to the environment for the desirable bacteria.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to compositions used as a prebiotic to promote the growth of beneficial bacteria by decreasing harmful bacteria populations and by releasing nutrients extracted from the harmful bacteria into the environment, thus decreasing bacterial crowding and providing nutrients from lysed unwanted bacteria for good bacteria in the digestive system of an individual. The prebiotics used in the disclosed compositions and methods are one or more bacteriophages, which have been discovered herein to act as prebiotics.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying FIGURE, which is incorporated in and constitutes a part of this specification, illustrates several aspects described below.

FIG. 1 is a graph showing the optical density (a measure of cell density) measured at intervals over 10 hours for various compositions disclosed herein.

DESCRIPTION

The materials, compositions, and methods described herein can be understood more readily by reference to the following detailed description of specific aspects of the disclosed subject matter and the Examples and FIGURE included herein.

Before the present materials, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a bacteriophage" includes mixtures of two or more such bacteriophages, reference to "an enzymes" includes mixtures of two or more such enzymes, reference to "the probiotic" includes mixtures of two or more such probiotics, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. "About" can mean within 5% of the stated value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "5" is disclosed, then "about 5" is also disclosed.

References in the specification and concluding claims to parts by weight of a particular element or component in a composition denotes the weight relationship between the element or component and any other elements or components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

Reference will now be made in detail to specific aspects of the disclosed materials, compounds, compositions, and methods, examples of which are illustrated in the accompanying Examples and FIGURE.

Methods

Microbial biomass makes up over 50% of colonic contents. There are more than 500 different culturable species of indigenous bacteria present in the adult large intestine comprising around 1012 bacteria per gram dry weight (Moore et al., Some current concepts in intestinal bacteriology, *Am. J. Clin. Nutr.* 31:S33-42, 1978; Moore, et al., Intestinal flora in health and disease, *Gastroenterology* 86:174-193, 1984). These microorganisms perform a host of useful functions, such as fermenting unused energy substrates, training the immune system, preventing growth of harmful, pathogenic bacteria, regulating the development of the gut, producing vitamins for the host (such as biotin and vitamin K), and producing hormones to direct the host to store fats. However, in certain conditions, some species are thought to be capable of causing disease by producing infection or increasing cancer risk for the host. (Guarner et al., Gut flora in health and disease, *Lancet* 361(9356):512-519, 2003.)

It is widely recognized that maintaining a proper balance of microorganisms in the intestine is essential to good health. Overpopulation of undesirable organisms modifies the intestinal environment to accommodate the undesirable species to the detriment of desirable organisms.

Probiotics are live microbial food supplements that beneficially affect the host human or animal by improving its intestinal microbial balance. The benefits of probiotics, including displacement of undesirable or pathogenic organism, resistance to colonization of undesirable organisms by competitive exclusion and stimulation of the immune system, have been documented in numerous articles and patents. To be effective, probiotics are taken in large quantities and over extended periods of time.

Prebiotics are food ingredients that stimulate the growth and/or activity of a probiotic in the digestive system so that the probiotic can provide the aforementioned benefits. Historically, prebiotics have been carbohydrates that are not digested directly by animals or humans but that can be carbohydrate sources for specific probiotic organisms and not fermented as well by undesirable organisms. The concept is that these carbohydrates preferentially feed the probiotic organisms giving them a competitive advantage over the undesirable organisms. To be effective, large repetitive doses of the prebiotics are required. It is also clear that large concentrations of other carbohydrates consumed with meals would reduce the effectiveness of these prebiotics.

Disclosed herein are methods of using compositions that comprise one or more lytic bacteriophages and one or more probiotic organisms. The bacteriophage component of the disclosed compositions acts as prebiotic to stimulate the growth of desirable organisms, including the probiotic component, as well as reduce the population of specific undesirable bacteria. The bacteriophage has specificity for one or more of the undesirable organisms. By weakening the population of the specific undesirable bacteria, the probiotic organisms can successfully compete and establish colonization producing an environment which is suitable for them but inhospitable to undesirable bacteria. The specific undesirable bacteria are lysed and their cellular contents are available as nutrients for probiotic organisms. No gasses or additional cellular material are produced thus the aforementioned undesired side effects (flatulence, bloating, and diarrhea) are avoided. The bacteriophage are very specific to the organism and as such do not directly affect any other organisms in the digestive tract or any probiotic. The dose of bacteriophage is quite small with no detectable impact on the material balance of the digestive process.

The disclosed methods can be achieved by administering a composition as disclosed herein, and that comprises one or more lytic bacteriophages and one or more probiotic organism. Further the disclosed methods can comprise the administration of a nutrition composition as herein described. Still further, disclosed herein is a method that comprises administering one or more lytic bacteriophages and then one or more probiotic organisms, or one or more probiotic organism and then one or more lytic bacteriophages.

Compositions

Disclosed herein are compositions for increasing the growth of desirable bacteria and probiotic bacteria in the digestive system of an individual. The disclosed compositions are nutritional compositions to be administered orally to an individual and can also contain vitamins, minerals, and nutrients for the individual. The disclosed compositions comprise one or more bacteriophages. These bacteriophages behave as prebiotics by stimulating the growth of the probiotic component of the disclosed compositions. The bacteriophages reduce the population of specific undesirable bacteria including but not limited to *bacteroides*, coliforms, lysteria, *helicobacter, salmonella* and *staphylococcus*. Each bacteriophage has specificity for an undesirable bacteria. By using the disclosed bacteriophages, specific undesirable bacteria are lysed and their cellular material is available as nutrients for the probiotic organism or endogenous. Further, by weakening the population of the specific undesirable bacteria, probiotic organisms can successfully compete and establish colonization producing an environment which is suitable for them but inhospitable to the undesirable organism. As such, the disclosed compositions can comprise one or more probiotic organisms, as disclosed elsewhere herein. No gasses or extra cellular material are produced; thus, the aforementioned undesired side effects are avoided. The bacteriophages of the disclosed compositions are very specific to the undesirable bacteria and, as such, do not directly affect any other organisms in the digestive tract or any probiotic. The dose of bacteriophage is quite small with no detectable impact on the material balance in the digestive process. Further by using the disclosed bacteriophages as a prebiotic, the use of more traditional prebiotics such as polysaccharides can be avoided.

Bacteriophages

Lytic bacteriophages are viruses that bind to specific bacterial cell surface receptors, inject their DNA, and take over the biosynthetic machinery of the bacterium to produce daughter phages, which are released via host lysis to re-peat the process in other target bacteria (Guttman et al., Basic phage biology. In: Bacteriophages: Biology and Applications. Kutter E andSulakvelidze A (eds). New York: CRC Press, 2004, pp. 29-66). Bacteriophages have been isolated from many environments, including the gastrointestinal tracts of food animals, where they are natural members of the microbial ecosystem (Orpin et al., The occurrence of bacteriophages in the rumen and their influence on rumen bacterial population, *Experientia* 30:1018-1020, 1974; Klieve et al., Morphological diversity of ruminal bacteriophages from sheep and cattle, *Appl Environ Microbiol* 54(6):1637-1641, 1988). This disclosed compositions comprise one or more lytic bacteriophages specifically targeted to assist probiotic organism in overcoming populations of harmful bacteria including but not limited to *Bacteroides, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio* and *Yersinia*.

In specific examples, the disclosed compositions comprise a lytic bacteriophage that is a member of the Bacteroidaceae family. In a preferred example, the bacteriophage is specific to *Bacteroides fragilis*. The *B. fragilis* group includes *B. fragilis* (causes the most clinical infections), *Bacteroides distasonis, Bacteroides ovatus, Bacteroides thetaiotaomicron*, and *Bacteroides vulgatus*. These bacteria are resistant to penicillins, mostly through the production of beta-lactamase. They are part of the normal GI florae (Brook, I., "Indigenous Microbial Flora of Humans," In: Surgical Infectious Diseases. 3rd Rd. Norwalk, Conn.: Appleton & Lange, 1995:37.) representing 30-50% of the fecal matter. They are responsible for 80% of anaerobic intra-abdominal infections. Enterotoxigenic *B. fragilis* (ETBF) is also a potential cause of diarrhea. (Durmaz, B., et al., "Prevalence of Enterotoxigenic *Bacteroides fragilis* in Patients with Diarrhea: a Controlled Study," *Anaerobe* 11(6):318-321, 2005.)

The Bacteroidaceae bacteriophages are part of the Siphoviridae family of double-stranded DNA viruses infecting only bacteria. The virons are nonenveloped and have a long filamentous non-contractile tail and an isometric capsid (morphotype B1). The icosahedral capsid (T=7) is 57 nm in diameter. It is composed of 72 capsomers that appear hexagonal in outline. The filamentous cross banded tail can reach to 570 nm. It has a width of ~8 nm and is non contractile. It has short terminal and subterminal fibers. The genome is double stranded and linear. It is typically ~50 kilobases in length and contains ~70 genes. The guanine+ cytosine content is ~52%.

In other examples, the disclosed compositions comprise a lytic bacteriophage that is specific to certain strains of *Escherichia coli* (*E. coli*). *E. coli* is a Gram-negative, rod-shaped bacterium that is commonly found in the lower intestine of warm-blooded organisms makes up about 0.1% of gut flora (Eckburg et al., Diversity of the Human Intestinal Microbial Flora, *Science.* 14(308):1635-1638, 2005). Most *E. coli* strains are harmless, but some serotypes can cause serious food poisoning in humans. Virulent strains of *E. coli* can cause gastroenteritis, urinary tract infections, and neonatal meningitis. In rare cases, virulent strains are also responsible for hemolytic-uremic syndrome, peritonitis, mastitis, septicemia and Gram-negative pneumonia.

Rakieten et al., Studies with bacteriophages active against mucoid strains of bacteria, *J. Bacteriol.* 40:529-545, 1940; Demerec et al., Bacteriophage-resistant mutants in *Escherichia coli*, Genetics 30:119-136, 1944. Delbrück, Bacterial viruses or bacteriophages, *Biol. Rev.* 21:30-40, 1946.

In the disclosed compositions and methods, a bacteriophage is used, which is not the same component as a lytic protein isolated from a bacteriophage.

Probiotic Organisms

The probiotic component of the disclosed compositions comprises live microorganisms that beneficially affect the host individual by displacement of undesirable or pathogenic bacteria and by creating an environment that resists colonization of the undesirable bacteria. When colonization of undesirable bacteria is present, probiotic organisms must compete with the established colonies. The combination of a beneficial bacteria with the disclosed bacteriophages can produce a symbiotic mixture.

In specific examples, the disclosed compositions comprise a probiotic organism that is a *Lactobacillus* species, such as *L. acidophilus, L. amylovorus, L. brevis, L. casei, L.* casei subsp. rhamnosus (Lactobacillus GG), L. caucasicus, L. crispatus, L. delbrueckii subsp. bulgaricus (L. bulgaricus), L. fermentum (L. fermenti), L. gasseri, L. helveticus, L. johnsonii, L. lactis, L. leichmannii, L. paracasei, L. plantarum, L. reuteri, and L. rhamnosus. In other examples, the disclosed compositions comprise a probiotic organism that is a Bifidobacterium species, such as B. adolescentis, B. bifidum, B. breve, B. infantis, B. lactis (B. animalis), B. licheniformis, and B. longum. In still other examples, the disclosed compositions comprise a probiotic organism that is a lactic acid bacteria such as Enterococcus faecium, Lactococcus lactis, Leuconstoc mesenteroides, Pediococcus acidilactici, Streptococcus thermophilus). In yet other examples, the disclosed compositions comprise a probiotic organism that is a nonlactic acid bacteria such as Bacillus subtilis, Saccharomyces boulardii, and Saccharomyces cerevisiae.

Additional Components

In further embodiments, the disclosed compositions can comprise other types of prebiotics. For example, the disclosed compositions can comprise inulin, fructooligosaccharides, galactooligosaccharides, xylooligosaccharides, polydextrose, lactulose, tagatose, isomaltooligosaccharides, soybean oligosaccharides, lactoferrin, and proanthocyanins. Though with the use of the disclosed bacteriophages, which act themselves as prebiotics, other prebiotics are not necessary.

The disclosed compositions can also include nutritional supplements, such as vitamins, minerals, trace elements, polyunsaturated fatty acids, antioxidants, amino acids, and the like.

Specific Combinations

Specific examples of suitable compositions disclosed herein include a bacteriophage that is specific to Bacteroides fragilis and/or E. coli and a probiotic selected from the group consisting of Lactobacillus (L.) acidophilus, L. amylovorus, L. brevis, L. casei, L. casei subsp. rhamnosus (Lactobacillus GG), L. caucasicus, L. crispatus, L. delbrueckii subsp. bulgaricus (L. bulgaricus), L. fermentum (L. fermenti), L. gasseri, L. helveticus, L. johnsonii, L. lactis, L. leichmannii, L. paracasei, L. plantarum, L. reuteri, and L. rhamnosus. In another specific example, the disclosed compositions can comprise a bacteriophage that is specific to Bacteroides fragilis and/or E. coli and a probiotic selected from the group consisting of Bifidobacterium (B.) adolescentis, B. bifidum, B. breve, B. infantis, B. lactis (B. animalis), B. licheniformis, and B. longum. In another specific example, the disclosed compositions can comprise a bacteriophage that is specific to Bacteroides fragilis and/or E. coli and a probiotic selected from the group consisting of Enterococcus faecium, Lactococcus lactis, Leuconstoc mesenteroides, Pediococcus acidilactici, and Streptococcus thermophilus. In another specific example, the disclosed compositions can comprise a bacteriophage that is specific to Bacteroides fragilis and/or E. coli and a probiotic selected from the group consisting of Bacillus subtilis, Escherichia coli strain nissle, Saccharomyces boulardii, and Saccharomyces cerevisiae.

Nutritional Compositions, Administration, Dosage

As described, the compositions disclosed herein can be provided in a nutritional composition. Depending on the intended mode of administration, the nutritional composition can be in the form of solid, semi-solid or liquid dosage forms, such as, for example, tablets, pills, capsules, powders, liquids, or suspensions, preferably in unit dosage form suitable for single administration of a precise dosage. The compositions will include an effective amount of the compositions described herein optionally in combination with a biologically acceptable carrier and, in addition, can include other flavorings, thickeners, chelating agents, binders, carriers, or diluents. By "biologically acceptable" is meant a material that is not biologically or otherwise undesirable, which can be administered to an individual along with the selected compositions without causing unacceptable biological effects or interacting in a deleterious manner with the other components of the nutritional composition in which it is contained.

As used herein, the term carrier encompasses any excipient, diluent, filler, salt, buffer, stabilizer, solubilizer, lipid, stabilizer, or other material well known in the art for use in nutritional formulations. The choice of a carrier for use in a composition will depend upon the intended route of administration for the composition. The preparation of nutritional acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of biologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). Further examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and animal oils (fish oil). Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Isotonic agents, for example, sugars, sodium chloride, and the like can also be included.

Solid dosage forms for oral administration of the compositions described herein include capsules, tablets, pills, powders, and granules. In such solid dosage forms, the compositions described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethylene glycols, and the like.

Solid dosage forms such as tablets, dragées, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compositions described herein include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Administration of the compositions described herein to an individual can be carried out using effective amounts of the compositions described herein for periods of time effective to treat a disease or infection. An individual can include both mammals and non-mammals. Mammals include, for example, humans; nonhuman primates, e.g. apes and monkeys; cattle; horses; sheep; rats; mice; pigs; and goats. Non-mammals include, for example, fish and birds. In a preferred embodiment, the individual is a human.

The effective amount of the compositions described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial inhibition or growth.

For the bacteriophage component of the disclosed compositions, they can be administered in an effective amount of from 1 colony forming unit (CFU)/mL to $1 \times 10^{13}$ plaque forming unit (PFU)/mL. 1 PFU/mL is approximately 1 phage/mL or 1 phage/g. In certain examples the bacteriophage component of the disclosed compositions can be administered in amounts of from about $1 \times 10^2$ to about $1 \times 10^{13}$, from about $1 \times 10^4$ to about $1 \times 10^{11}$, from about $1 \times 10^6$ to about $1 \times 10^{10}$, from about $1 \times 10^3$ to about $1 \times 10^9$, from about $1 \times 10^5$ to about $1 \times 10^7$, or from about $1 \times 10^7$ to about $1 \times 10^{11}$ PFU/mL or PFU/g. In further examples the bacteriophage can be administered in amounts of from about $1 \times 10^4$ to about $1 \times 10^6$ PFU/mL or PFU/g. In still further examples, the bacteriophage component can be administered in amounts of at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, or $1 \times 10^{13}$ PFU/mL or PFU/g.

Those of skill in the art will understand that the specific dose level and frequency of dosage for any particular subject can be varied and will depend upon a variety of factors, including the activity of the specific composition employed, the metabolic stability and length of action of that composition, the species, age, body weight, general health, sex and diet of the subject, the mode and time of administration, rate of excretion, active combination, and severity of the particular condition.

The examples below are intended to further illustrate certain aspects of the methods and compounds described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations that are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the disclosed process. Only reasonable and routine experimentation will be required to optimize such process conditions.

In vitro studies to determine the ability of bacteriophage to allow specific changes, both in the composition and/or activity in gastrointestinal microflora, were done under physiological conditions of the small intestine (37° C. and pH 6.8). The bacteria selected for testing included three species of *Bacteroides*, namely strains of *fragilis*, uniformis and thetaiotaomicron and two species of *E. coli*, namely strains of *E. coli* B and C and five strains of probiotics:

Bacillus subtilis, Lactobacillus paracasei, Lactobacillus lactis, Bifidobacterium breve and Bifidobacterium longum.

Example 1

Bacteroides fragilis, Bacteroides uniformis, Bacteroides thetaiotaomicron and four strains of probiotics; Lactobacillus paracasei, Lactobacillus lactis, Bifidobacterium breve and Bifidobacterium longum (all Bacteroides strains purchased from ATCC) were tested in vitro. Frozen permanents of each bacterial strain were streaked for single colonies using Bile Esculin agar or nutrient agar warmed prior to use. For fresh inoculants, single bacterial cells were re-streaked on a Bile Esculin agar. The bacteriophage was propagated from bacteroides fragilis after 16-20 hours of bacterial growth, 16000 rpm cell clearing spin for 30 minutes and collection of the supernatant. Bacteriophage were concentrated using an Amicon Ultra-15.50 kDa cutoff concentrator, titers were determined by counting plaques from serial dilutions using the bacterial host strain. The Bacteroides fragilis bacteriophage (FBP) Cocktail was diluted to $1 \times 10^6$ PFU/mL.

Bacterial cells of several fresh colonies were incubated in 50 mLs of nutrient broth (1% glucose) until the culture reached an optical density of 0.2. For anaerobic growth, 0.2 cultures were divided into flasks and purged with a 3-5 second shot of nitrogen, bacteriophage were quickly added at a multiplicity of infection (MOI) of 1 to one set and broth to the other for a control to each flask, sealed and put back on the shaker. Anaerobic samples were opened once, tested and discarded. The optical density was measured at intervals over 10 hours. See FIG. 1.

The addition of the FBP to the Bacteroides fragilis culture rapidly reduced the population while the addition of FBP had no effect on any of the other organisms tested.

Example 2

Bacteroides fragilis and four strains of probiotics; Lactobacillus paracasei, Lactobacillus lactis, Bifidobacterium breve and Bifidobacterium longum (all Bacteroides strains purchased from ATCC) were tested in vitro. Bacteroides is the dominate bacteria in the human gut, while most of the time, most of the strains of Bacteroides are symbiotic, certain bacteroides strains can be pathogenic. One of the main bacteroides strains known to cause pathogenicity in humans is bacteroides fragilis, which can take over the gastrointestinal tract robbing nutrients and crowding out good bacteria. For that reason, a prebiotic bacteriophage was chosen for its ability to quickly and efficiently lyse Bacteroides fragilis exclusively, providing good bacteria nutrients while maintaining a healthy natural gut flora. Frozen permanents of each bacterial strain were streaked for single colonies using Bile Esculin agar or nutrient agar warmed prior to use. For fresh inoculants, single bacterial cells were re-streaked on a Bile Esculin agar. The bacteriophage was propagated from Bacteroides fragilis after 16-20 hours of bacterial growth, 16000 rpm cell clearing spin for 30 minutes and collection of the supernatant. Bacteriophage were concentrated using an Amicon Ultra-15.50 kDa cutoff concentrator, titers were determined by counting plaques from serial dilutions using the bacterial host strain. The Bacteroides fragilis bacteriophage (FBP) Cocktail was diluted to $1 \times 10^6$ PFU/mL.

Bacterial cells of several fresh colonies were incubated in 50 mLs of nutrient broth (1% glucose) until the culture reached an optical density of 0.2. For anaerobic growth, 0.2 cultures were divided into flasks and purged with a 3-5 second shot of nitrogen, bacteriophage were quickly added at a multiplicity of infection (MOI) of 1 to one set and broth to the other for a control to each flask, sealed and put back on the shaker. Anaerobic samples were opened once, tested and discarded. Probiotic alone, with bacteroides, with bacteroides and FBP cocktail together and with FBP cocktail were mixed and allowed to grow for indicated time period in a shaker bath at 37° C. and pH 6.8. One milliliter samples were taken and diluted several times in Hardy Diagnostic phosphate buffer and plated on selected media for each type of probiotic and for bacteroides on bacteroides bile esculin plates (PML microbiologicals) and the selected media alone as a control. Bacteroides that grew on the selected media for the probiotic was subtracted out from the total plate count of the mixture. MRS agar (Neogen) plates were used for quantification of Lactobacillus strains, Bifidobacterium agar (Hardy Diagnostics) were used for the quantification of Bifidobacterium strains. Experiments were done in triplicate, multiple dilutions were done and 5 or more plates were averaged to determine bacterial counts. Test counts were subtracted out from control plates for final sample counts. See Table 1.

TABLE 1

| Nutrient Broth | | |
|---|---|---|
| | CFU/ml after 5 hr | |
| Strains | | Bacteroides Fragilis |
| L. Paracasei | | |
| Individual (anaerobic) | $1 \times 10^3$ | $4 \times 10^3$ |
| L. Paracasei + Bacteroides Fragilis | $2 \times 10^2$ | $1 \times 10^2$ |
| L. Paracasei + Bacteroides Fragilis + FBP | $7 \times 10^3$ | 5 |
| L. lactis | | |
| Individual (anaerobic) | $9 \times 10^3$ | $1 \times 10^4$ |
| L. Lactis + Bacteroides Fragilis | $7 \times 10^2$ | $3 \times 10^3$ |
| L. Lactis + Bacteroides Fragilis + FBP | $2 \times 10^4$ | 0 |
| B. Longum | | |
| Individual (anaerobic) | $2 \times 10^3$ | $6 \times 10^3$ |
| B. Longum + Bacteroides Fragilis | $1 \times 10^2$ | $1 \times 10^3$ |
| B. Longum + Bacteroides Fragilis + FBP | $7 \times 10^3$ | 12 |
| B. Breve | | |
| Individual (anaerobic) | $1 \times 10^4$ | $9 \times 10^3$ |
| B. Breve + Bacteroides Fragilis | $4 \times 10^2$ | $7 \times 10^3$ |
| B. Breve + Bacteroides Fragilis + FBP | $5 \times 10^4$ | 6 |

Mixed cultures of Bacteroides fragilis and each of the probiotics reduced the growth of both the probiotic and of the Bacteroides as compared with the pure cultures. The addition of FPB cocktail essentially eliminated the Bacteroides fragilis while significantly increasing the growth of each probiotic over the controls. These results indicate that the lytic activity on the Bacteroides provides nutrients which stimulate the growth of each of the probiotics tested.

Example 3

Bacterial cells of several fresh colonies were incubated in 50 mLs of nutrient broth (1% glucose) until the culture reached an optical density of 0.2. The bacteria was spun down and re-suspended in minimal media with 1% glucose, 1% inulin or 1% Isomalta-oligosaccharide as the sole carbon source. For anaerobic growth, 0.2 cultures were divided into flasks and purged with a 3-5 second shot of nitrogen, bacteriophage were quickly added at a multiplicity of infection (MOI) of 1 to one set and broth to the other for a control to each flask, sealed and put back on the shaker. Anaerobic samples were opened once, tested and discarded. Probiotic alone, with *bacteroides*, with *bacteroides* and FBP cocktail together and with FBP cocktail were mixed and allowed to grow for indicated time period in a shaker bath at 37° C. and pH 6.8. One milliliter samples were taken and diluted several times in Hardy Diagnostic phosphate buffer and plated on selected media for each type of probiotic and for *bacteroides* on *bacteroides* bile esculin plates (PML microbiologicals) and the selected media alone as a control. *Bacteroides* that grew on the selected media for the probiotic was subtracted out from the total plate count of the mixture. MRS agar (Neogen) plates were used for quantification of *Lactobacillus*, *Bifidobacterium* agar (Hardy Diagnostics) were used for the quantification of *Bifidobacterium*. Experiments were done in triplicate, multiple dilutions were done and 5 or more plates were averaged to determine bacterial counts. Test counts were subtracted out from control plates for final sample counts. See Table 2.

TABLE 2

| MM + Inulin Strain(s) | CFU/ml after 48 hours | |
|---|---|---|
| | L. Paracasei | Bacteroides Fragilis |
| Individual (anaerobic) | 2730 | 0 |
| L. Paracasei + Bacteroides Fragilis | 2850 | 0 |
| L. Paracasei + Bacteroides Fragilis + FBP | 2650 | 0 |
| Strain(s) | B. Longum | Bacteroides Fragilis |
| Individual (anaerobic) | 2590 | 0 |
| B. Longum + Bacteroides Fragilis | 2340 | 0 |
| B. Longum + Bacteroides Fragilis + FBP | 2570 | 0 |

| MM + Vitafiber Strain(s) | CFU/ml after 48 hours | |
|---|---|---|
| | L. Paracasei | Bacteroides Fragilis |
| Individual (anaerobic) | 3610 | 1240 |
| L. Paracasei + Bacteroides Fragilis | 2780 | 970 |
| L. Paracasei + Bacteroides Fragilis + FBP | 3830 | 0 |
| Strain(s) | B. Longum | Bacteroides Fragilis |
| Individual (anaerobic) | 3980 | 1060 |
| B. Longum + Bacteroides Fragilis | 2790 | 780 |
| B. Longum + Bacteroides Fragilis + FBP | 4120 | 0 |

| Nutrient + Inulin Strain(s) | CFU/ml after 48 hours | |
|---|---|---|
| | L. Paracasei | Bacteroides Fragilis |
| Individual (anaerobic) | $1 \times 10^6$ | $9 \times 10^4$ |
| L. Paracasei + Bacteroides Fragilis | $9 \times 10^3$ | $6 \times 10^2$ |
| L. Paracasei + Bacteroides Fragilis + FBP | $8 \times 10^6$ | 16 |
| Strain(s) | L. Paracasei | Bacteroides Fragilis |
| Individual (anaerobic) | $7 \times 10^6$ | $8 \times 10^4$ |
| B. Longum + Bacteroides Fragilis | $2 \times 10^4$ | $1 \times 10^3$ |
| B. Longum + Bacteroides Fragilis + FBP | $1 \times 10^7$ | 23 |

| Nutrient + Vitafiber Strain(s) | CFU/ml after 48 hours | |
|---|---|---|
| | L. Paracasei | Bacteroides Fragilis |
| Individual (anaerobic) | $3 \times 10^6$ | $6 \times 10^5$ |
| L. Paracasei + Bacteroides Fragilis | $4 \times 10^4$ | $5 \times 10^3$ |
| L. Paracasei + Bacteroides Fragilis + FBP | $4 \times 10^7$ | 10 |
| Strain(s) | B. Longum | Bacteroides Fragilis |
| Individual (anaerobic) | $1 \times 10^6$ | $3 \times 10^5$ |
| B. Longum + Bacteroides Fragilis | $1 \times 10^4$ | $7 \times 10^3$ |
| B. Longum + Bacteroides Fragilis + FBP | $8 \times 10^6$ | 8 |

The results indicate that the bacteriophage had no negative effect on either the *Lactobacillus* or *Bifidobacterium*. Neither inulin nor Isomalta-oligosaccharide alone were good nutrients for any of the organisms. In nutrient broth with either inulin or Isomalta-oligosaccharide added the *Bacteroides* and probiotics inhibit each other's growth. In nutrient broth with either inulin or Isomalta-oligosaccharide added, in the presence of the bacteriophage, the *Bacteroides fragilis* population is reduced by several logs while the probiotic population is increased about 3 logs and about one log over the probiotic controls. This corresponds to the previous experiment and provides further evidence that the lysed *bacteroides* is being used by the probiotics as nutrient.

Example 4

Four bacteriophage were chosen for their ability to quickly and efficiently lyses several strains of *E. coli* including *E. coli* B, five Enterotoxigenic *Escherichia coli*, or ETEC, that produces heat stable toxin (ST), five ETEC *E. coli* strains that produce heat labile (LT), five that produce both ST and LT toxins and *E. coli* O157:H7.

The bacteriophage were propagated from non-pathogenic *E. coli* B, C or K12 (all strains were a gift from Texas A&M University) after 12-16 hours of bacterial growth, 16000 rpm cell clearing spin for 30 minutes and collection of the supernatant. Bacteriophage were concentrated using an Amicon Ultra-15.50 kDa cutoff concentrator, titers were determined by counting plaques from serial dilutions using the bacterial host strain. The *E. coli* bacteriophage Cocktail (EBP) were diluted to $1 \times 10^6$ PFU/mL and mixed at a 1:1:1:1 ratio.

Bacterial cells of several fresh colonies were incubated in 50 mLs of nutrient broth (1% glucose) until the culture reached an optical density of 0.2. For competition experiments, each bacteria was grown to an O.D. of 0.2, halved and added together. Bacteriophages were quickly added at a multiplicity of infection (MOI) of 1 to one set and broth to the other for a control. For anaerobic growth, 0.2 cultures were divided into 9 flasks and purged with a 5 second shot of nitrogen, bacteriophage (MOI 1) and broth were divided up and added to each flask, sealed and put back on the shaker. Anaerobic samples were opened once, tested and discarded. Probiotic alone, probiotic with *E. coli*, probiotic with both *E. coli* and EBP together and probiotic with only EBP were mixed and allowed to grow for 1 hour in a shaker bath at 37° C. and pH 6.8. One milliliter samples were taken and diluted several times in Hardy Diagnostic phosphate buffer and plated on selected media for each type of probiotic and for *E. coli* on 3M *E. coli* plates and the selected media alone as a control. *E. coli* that grew on the selected media for the probiotic was subtracted out from the total plate count of the mixture. Nutrient agar (Hardy Diagnostics) plates were used for quantification of *Bacillus subtilis*, MRS agar (Neogen) plates were used for quantification of *Lactobacillus paracasei* and *Lactobacillus lactis*, *Bifidobacterium* agar (Hardy Diagnostics) were used for the quantification of *Bifidobacterium breve* and *Bifidobacterium longum*. Experiments were done in triplicate, multiple dilutions were done and 5 or more plates were averaged to determine bacterial counts.

Example 4a

*Bacillus subtilis* was evaluated as described above both aerobically and anaerobically. Under aerobic conditions, *E. coli* reduced the probiotic by almost 2 logs. With EPB added the *E. coli* was reduced by 10 logs while allowing the probiotic to increase 2 logs. Under anaerobic *E. coli* reduced the probiotic by 1 log. With EPB added *E. coli* was reduced by 1 log while allowing the probiotic to increase almost 2 logs (Table 3).

TABLE 3

|  | Log CFU | |
| --- | --- | --- |
|  | *Bacillus Subtilis* | *E. coli* B |
| Individual (aerobic) | 7.3 | 9.8 |
| *B. Subtilis* + *E. coli* B(aerobic) | 5.6 | 7.8 |
| *B. Subtilis* + *E. coli* B + EBP(aerobic) | 7.7 | 0.0 |
| Individual (anaerobic) | 3.0 | 4.5 |
| *B. Subtilis* + *E. coli* B(anaerobic) | 1.9 | 3.0 |
| *B. Subtilis* + *E. coli* B + EBP(anaerobic) | 3.6 | 2.0 |

Example 4b

*Lactobacillus paracasei* was evaluated as described above both aerobically and anaerobically. Under aerobic conditions, *E. coli* reduced the probiotic by almost 3 logs. With EPB added the *E. coli* was reduced by 7 logs while allowing the probiotic to increase 1 log. Under anaerobic *E. coli* reduced the probiotic by over 1 log. With EPB added *E. coli* was reduced by over 2 log while allowing the probiotic to increase almost 1 log (Table 4).

TABLE 4

|  | Log CFU | |
| --- | --- | --- |
|  | *L. Paracasei* | *E. coli* B |
| Individual (aerobic) | 5.5 | 9.0 |
| *L. Paracasei* + *E. coli* B (aerobic) | 2.8 | 7.0 |
| *L. Paracasei* + *E. coli* B + EBP (aerobic) | 4.0 | 0.5 |
| Individual (anaerobic) | 3.0 | 6.0 |
| *L. Paracasei* + *E. coli* B (anaerobic) | 1.5 | 5.0 |
| *L. Paracasei* + *E. coli* B + EBP (anaerobic) | 2.8 | 2.5 |

Example 4c

*Lactobacillus lactis* was evaluated as described above anaerobically. *E. coli* reduced the probiotic by almost 2 logs. In presence of the EPB the *E. coli* was reduced by 3 logs while allowing the probiotic to increase 1 log (Table 5).

TABLE 5

|  | Log CFU | |
| --- | --- | --- |
|  | *L. Lactis* | *E. coli* B |
| Individual (anaerobic) | 3.8 | 5.9 |
| *L. Lactis* + *E. coli* B | 2.0 | 4.0 |
| *L. Lactis* + *E. coli* B + EBP | 3.0 | 1.0 |

Example 4d

*Bifidobacterium longum* was evaluated as described above anaerobically. *E. coli* reduced the probiotic by almost 2 logs. In presence of the EPB the *E. coli* was reduced by 3 log while allowing the probiotic to increase 1 log (Table 6).

TABLE 6

|  | Log CFU | |
| --- | --- | --- |
|  | *B. Longum* | *E. coli* B |
| Individual (anaerobic) | 4.3 | 5.9 |
| *B. Longum* + *E. coli* B | 2.5 | 4.3 |
| *B. Longum* + *E. coli* B + EBP | 3.8 | 1.0 |

Example 4e

*Bifidobacterium Breve* was evaluated as described above anaerobically. *E. coli* reduced the probiotic by almost 2 logs. In presence of the EPB the *E. coli* was reduced by 2 log while allowing the probiotic to increase 1 log (Table 7).

TABLE 7

|  | Log CFU | |
| --- | --- | --- |
|  | *B. Breve* | *E. coli* B |
| Individual (anaerobic) | 4.5 | 5.9 |
| *B. Breve* + *E. coli* B | 2.8 | 4.7 |
| *B. Breve* + *E. coli* B + EBP | 4.0 | 2.3 |

In each example, the *E. coli* population inhibited the growth of the probiotic organism. Also in every case, the addition of EPB reduced the *E. coli* by more than 98% while increasing the probiotic population by more than 10 fold.

Clearly the use of EPB either as a symbiotic mixture or used separately but simultaneously provides a significant improvement in probiotic growth.

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A method for increasing the growth of probiotic organisms in the digestive system of an individual, comprising administering a composition comprising a lytic bacteriophage of the Siphoviridae family and that is specific to *Bacteroides fragilis* and one or more probiotic organisms chosen from *Lactobacillus* species and *Bifidobacterium* species.

2. The method of claim 1, wherein the composition comprises one or more additional bacteriophages specific to *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio* and *Yersinia*.

3. The method of claim 1, wherein the composition further comprises one or more bacteriophages specific to *E. coli* B, Enterotoxigenic *E. coli* (ETEC), and *E. coli* O157:H7.

4. The method of claim 1, wherein the probiotic organism is a *Lactobacillus* species.

5. The method of claim 1, wherein the probiotic organism is *L. acidophilus, L. amylovorus, L. brevis, L. casei, L. casei* subsp. *rhamnosus* (*Lactobacillus* GG), *L. caucasicus, L. crispatus, L. delbrueckii* subsp. *bulgaricus* (*L. bulgaricus*), *L. fermentum* (*L. fermenti*), *L. gasseri, L. helveticus, L. johnsonii, L. lactis, L. leichmannii, L. paracasei, L. plantarum, L. reuteri,* or *L. rhamnosus*.

6. The method of claim 1, wherein the probiotic organism is a *Bifidobacterium* species.

7. The method of claim 1, wherein the probiotic organism is one or more *B. adolescentis, B. bifidum, B. breve, B. infantis, B. lactis* (*B. animalis*), *B. licheniformis,* and *B. longum*.

8. The method of claim 1, wherein the probiotic organism is one or more *Enterococcus faecium, Lactococcus lactis, Leuconstoc mesenteroides, Pediococcus acidilactici,* and *Streptococcus thermophilus*.

9. The method of claim 1, wherein the probiotic organism is *Bacillus subtilis, Saccharomyces boulardii,* or *Saccharomyces cerevisiae*.

10. The method of claim 1, wherein the composition further comprises inulin, fructooligosaccharides, galactooligosaccharides, xylooligosaccharides, polydextrose, lactulose, tagatose, isomaltooligosaccharides, soybean oligosaccharides, lactoferrin, and proanthocyanins.

11. The method of claim 1, wherein the amount of bacteriophage in the composition is at least $1 \times 10^4$ CFU/g.

* * * * *